(12) United States Patent
Kawashima et al.

(10) Patent No.: US 6,284,745 B1
(45) Date of Patent: Sep. 4, 2001

(54) GEL COMPOSITIONS

(75) Inventors: Susumu Kawashima; Yoshifumi Murata, both of Ishikawa (JP)

(73) Assignee: Meiji Milk Products Co., Ltd. (JP)

( * ) Notice: Subject to any disclaimer, the term of this patent is extended or adjusted under 35 U.S.C. 154(b) by 0 days.

(21) Appl. No.: 09/396,988

(22) Filed: Sep. 14, 1999

(30) Foreign Application Priority Data

Mar. 4, 1999 (JP) .................................... 11/057094

(51) Int. Cl.⁷ .................................................... A61K 31/70
(52) U.S. Cl. ................................................. 514/55; 514/54
(58) Field of Search ......................................... 514/54, 55

(56) References Cited

FOREIGN PATENT DOCUMENTS

WO 98/51348 * 11/1998 (WO).

OTHER PUBLICATIONS

Tabata, Y. et al. (1998) "A sustained release cell growth factor from a biodegradable hydro–gel of polymer complex" Pharmaceutical Society of Japan. The 118th meeting, abstract No. 31–YC–10–1.

Sasaki, N. et al. (1998) "IH20 Preparation of buoyant alginate gel bead and the functions" *Polymer Preprints* 47(12):2996–2997.

Sezaki, H. (1989) "An example of release controlled pharmaceutical formulations" *Development of Medicine* 13:163.

* cited by examiner

*Primary Examiner*—Elli Peselev
(74) *Attorney, Agent, or Firm*—Saliwanchik, Lloyd & Saliwanchik

(57) ABSTRACT

The present invention provides a sustained-release composition obtained by gelating a compound such as a drug together with an oil or polysaccharide. This composition enables excellent sustained release of a contained compound such as a drug. Orally administered, the gel composition can stay in the stomach for a prolonged period by adjusting its specific gravity by varying the amount of oil or polysaccharide in the composition.

5 Claims, 20 Drawing Sheets

GEL COMPOSITIONS

FIELD OF THE INVENTION

The present invention relates to a gel composition comprising a compound to be sustainedly released, and an oil or a polysaccharide, which are especially applicable to the fields of medicine and health foods.

BACKGROUND OF THE INVENTION

An orally administered pharmaceutical preparation passes through the esophagus and releases the contained drug while moving in the digestive tract. Since this digestive tract has a certain length, it will take a certain period for the pharmaceutical preparation to move along the tract, wherein the pH of digestive juice varies from acidic, weakly acidic to weakly basic. Some drug is metabolized in the digestive tract, while almost all drugs are metabolized more or less after they are absorbed into the body. In order to secure the desirable pharmaceutical effect with high safety, release of the drug from the pharmaceutical preparation should be precisely controlled. For this purpose, many techniques have been developed for the controlled release of drugs from oral pharmaceutical preparations (cf. "Iyakuhin no Kaihatsu, Yakubutsu Soutatsu-hou (Drug Delivery Method" Development of Medicine), Vol. 13, Hirokawa Shoten).

However, techniques used in the conventional pharmaceutical preparation for controlled release are mainly for the sustained release of the drug while it passes through the small intestine, the principal absorption site for many drugs. Therefore, these preparations, especially those for treating stomach disorders, cannot be expected to stay at a high concentration over a long period at the affected site.

There have been several reports on the endogastric residence of drugs. For example, a pharmaceutical preparation containing a drug and an additive to generate carbon dioxide gas, which enables the drug to float on the gastric juice utilizing the buoyancy of the generated gas in the stomach (Watanabe et al. Yakuzaigaku (Pharmaceutics), Vol. 153, No. 1, 1–7 (1993)), and a pharmaceutical preparation containing a drug and a viscous solution (e.g. an aqueous solution of sodium alginate), which can prolong the time of endogastric residence of the drug upon oral administration (Yasuhiko Tabata et al. Sustained-release of the cell growth factor in the biodegradable hydrogel using an intermolecular complex of macromolecules, the Pharmaceutical Society of Japan, the 118th Annual Assembly, Abstracts 31-TC-10-1, 1988) have been proposed. In addition, the development of a carrier for sustained release of drugs using a hydrogel of gelatin cross-linked with glutaraldehyde has been reported (Yasuhiko Tabata et al., Sustained release of the cell growth factor from biodegradable hydrogel using an intermolecular complex of macromolecules, the Pharmaceutical Society of Japan, the 118th Annual Assembly, Abstracts 31-TC-10-1, 1988). Including the above reports, no sustained-release agents comprising oil or polysaccharide have been hitherto reported.

SUMMARY OF THE INVENTION

An objective of the present invention is to provide a gel composition that has excellent sustained-release characteristics for contained compounds such as drugs and enhances endogastric residence of the compound by adjusting its specific gravity.

The present inventors studied how to solve the above-described problems and found that a composition obtained by gelating a compound such as a drug together with oil or polysaccharide had excellent sustained-release characteristics for said compound. Furthermore, the present inventors discovered that, by adjusting the specific gravity of this gel composition relative to water through alteration of the amount of oil or polysaccharide in this gel composition, it is possible to prolong the gel's endogastric residence when said gel composition is orally administered.

Specifically, the present invention relates to a gel composition that has excellent sustained-release characteristics for a contained compound such as a drug and is capable of enhancing its endogastric residence by adjusting its specific gravity. More specifically, the present invention relates to:

(1) a gel composition comprising a compound to be sustainedly released, and an oil or polysaccharide;

(2) the gel composition according to (1), wherein said gel is alginate gel;

(3) the gel composition according to (1), wherein said oil is selected from the group consisting of olive oil, corn oil, and sesame oil;

(4) the gel composition according to (1), wherein said polysaccharide is chitosan;

(5) the gel composition according to (1), wherein said compound to be sustainedly released is a drug; and (6) the gel composition according to (5), wherein said drug is for treating diseases of digestive organs.

DETAILED DESCRIPTION OF THE INVENTION

Figure 1:
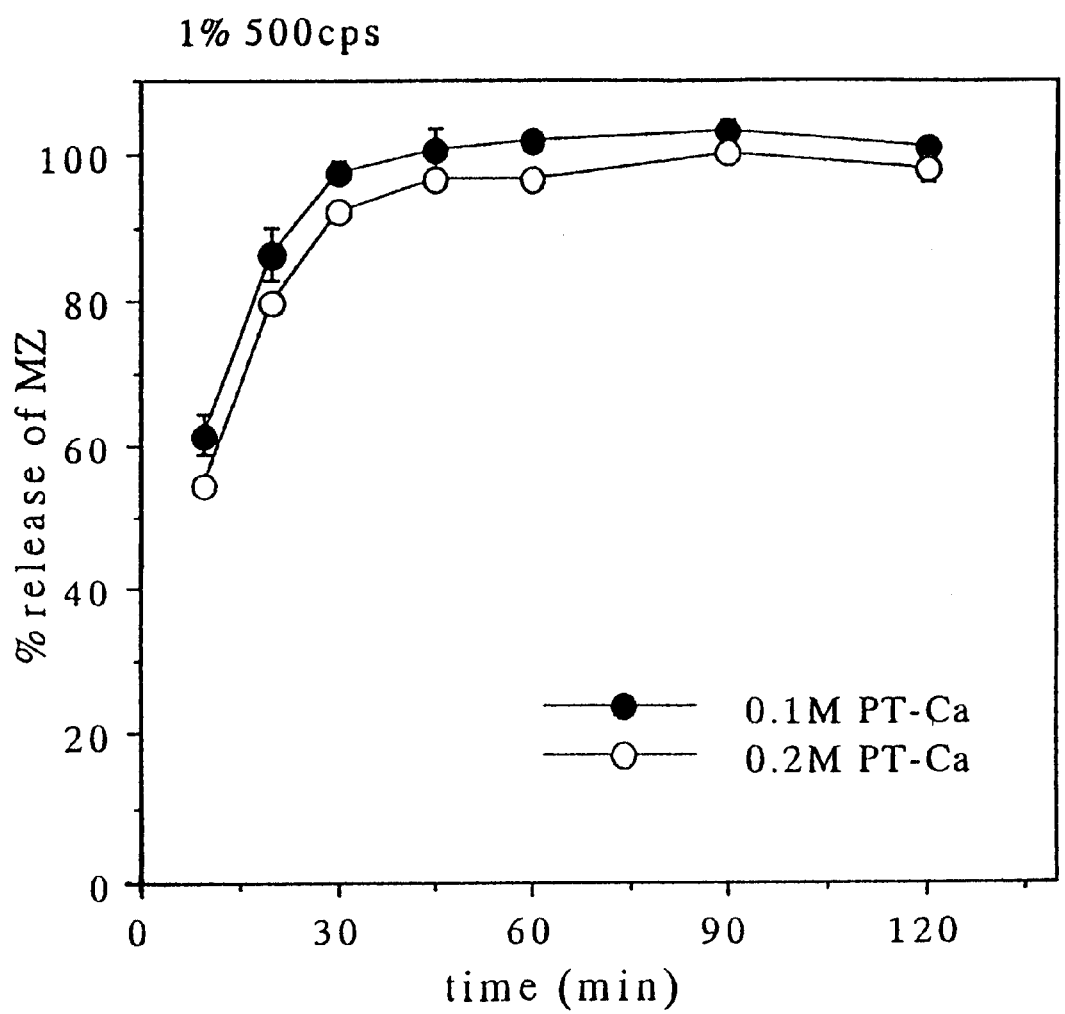
FIG. 1 is a graph showing the sustained-release characteristics of alginate gel containing metronidazole (but no oil).

The present invention relates to a gel composition comprising a compound to be sustainedly released, and an oil or polysaccharide. There is no particular limitation in the type of compound to be sustainedly released using the gel composition according to this invention. When the gel composition of this invention is used as a pharmaceutical preparation, various drugs can be used. The specific gravity of the gel composition of the present invention relative to water can be adequately altered by adjusting the amount of oil or polysaccharide contained therein so as to improve endogastric residence of the incorporated compound when administered orally. Drugs to be contained in the gel composition with the improved endogastric residence are preferably those for treating diseases of digestive organs, especially the upper digestive organs (e.g. upper digestive tract ulcer caused by *Helicobacter pyroli*, etc.), such as metronidazole, omeprazole, bismuth, tetracycline, and amoxicillin. "Upper digestive organs" means the upper part of digestive system including the stomach and small intestine.

Furthermore, oleaginous compounds such as DHA, EPA, and vitamin E can be incorporated into the gel composition of this invention. Such a composition can be applied to not only medicines but also health foods.

There is no particular limitation in the type of oils used for preparing the gel composition of this invention as long as they have a lower specific gravity than water. However, oils such as olive oil and corn oil that hardly leak during the preparation of alginate gel are preferred. The amount of oil used to prepare the gel composition of this invention is usually 0.1 to 30% (w/w).

Although the type of polysaccharide used for preparing the gel of this invention is not limited as long as it provides the gel with buoyancy, chitosan is especially preferred. The amount of the polysaccharide contained in the gel composition may be varied depending on amounts of other ingredients of the composition. One skilled in the art can easily determine the amount of the polysaccharide that provides the gel composition with buoyancy.

The type of gels used for preparing the gel composition of this invention is not particularly limited as long as it can stabilize an oil or polysaccharide having a low specific gravity. However, alginate gel beads are preferable. The amount of the alginate gel beads contained in the gel composition is 0.5 to 20% (w/w), preferably 0.7 to 1.5% (w/w), more preferably 0.8 to 1.2% (w/w), and most preferably about 1%.

The gel composition of the present invention can be prepared as follows. The alginate gel can be prepared by adding an aqueous solution of sodium alginate containing a compound to be sustainedly released and an oil or polysaccharide dropwise to an aqueous solution of a gelation agent such as calcium pantothenate. This procedure can form gel instantly. In this case, the concentration of calcium pantothenate to be used is usually about 0.02 to about 0.2 M, and preferably about 0.1 to about 0.2 M. The pH of the reaction system is usually about 4.0 to about 7.0, and preferably about 4.5 to about 6.5. When gels other than alginate gel are used, the pH should be in the acidic to neutral range so that its gelation is not disturbed.

The gel composition of the present invention can be orally administered to a human subject. When the gel composition of this invention is used as a pharmaceutical composition, about 200 mg of a drug can be contained in 2.5 g of the hydrogel. As a result, a single dose of a desired drug can usually be achieved by administering 2 to 3 g of the hydrogel composition.

The present invention provides a compound to be sustainedly released and a gel composition comprising an oil or polysaccharide. The gel composition of this invention has excellent sustained-release characteristics for compounds such as drugs incorporated therein, and prolongs residence of the drug in the stomach by adjusting its specific gravity when orally administered. Therefore, this composition is especially useful for treating diseases of digestive organs.

The following describes the present invention in more detail with reference to examples, but is not to be construed as being limited thereto.

Comparative Example 1

Preparing Alginate Gel Containing Metronidazole and its Sustained-release Characteristics The sustained-release characteristics of metronidazole in the alginate gel without oil was examined. First, a 1% sodium alginate solution (2.5 g) (SIGMA Chemical Co., MO, USA) containing metronidazole (0.25 g) was added drop-wise to 0.1 M or 0.2 M calcium pantothenate solution (gelation agent) (10 ml) and allowed to stand for 24 h to prepare hydrogel beads. Hydrogel beads thus prepared were subjected to the drug release test according to the second method of the dissolution test (paddle method, 150 rotations, 37° C.) in the Japanese Pharmacopoeia using 500 ml of artificial gastric juice (Solution 1 (pH 1.2) used in the disintegration test, the Japanese Pharmacopoeia) that had been prewarmed at 37±0.5° C. Samples (0.5 ml each) were periodically collected from the artificial gastric juice to which gel beads had been added and diluted 20-fold with the artificial gastric juice (9.5 ml). The absorbance at 277 mm was then measured with a spectrophotometer. The drug concentration was calculated from the previously prepared calibration curve of the contained drug to obtain its released amount (FIG. 1). No differences in the sustained release of metronidazole were observed between gel beads prepared using 0.1 M and 0.2 M calcium pantothenate as the gelation agent. All of the metronidazole was released in about 30 min.

EXAMPLE 1

Figure 2:
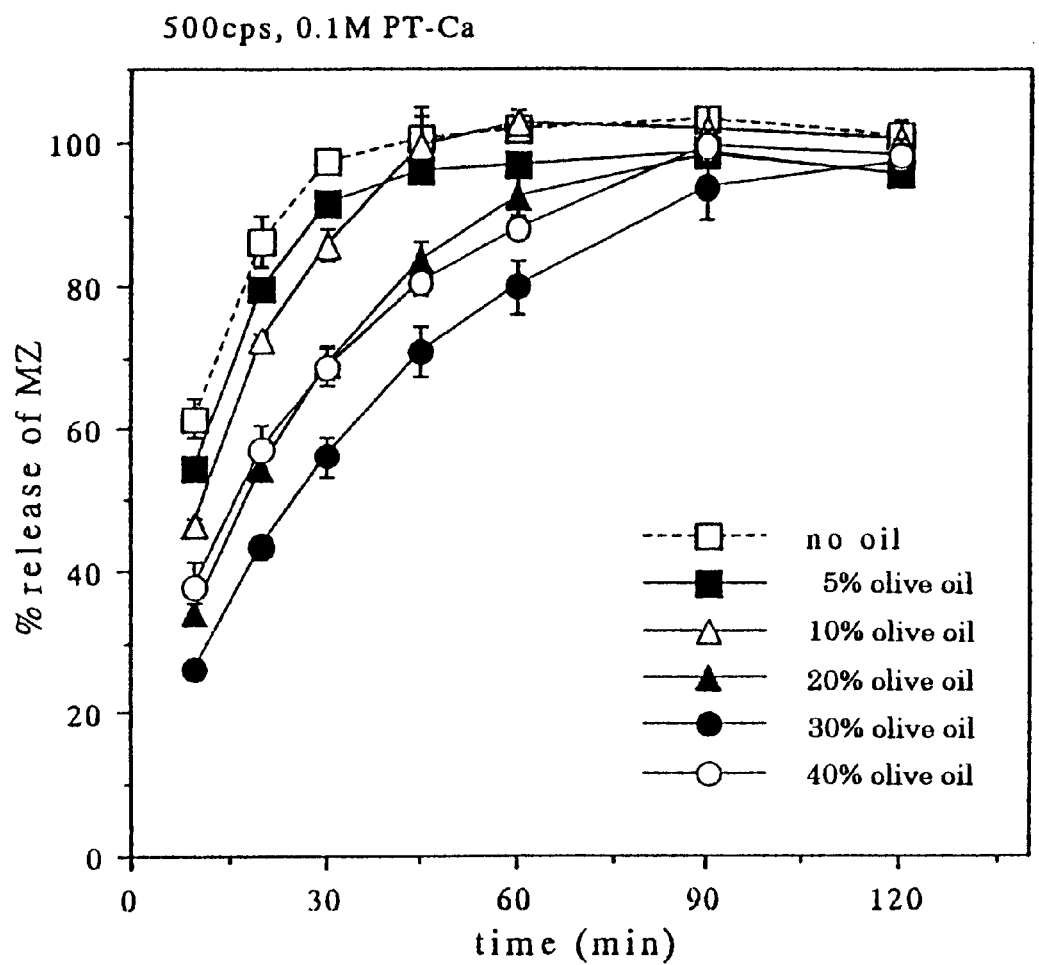
FIG. 2 is a graph showing the sustained-release characteristics of alginate gel containing metronidazole and various concentrations of olive oil. Calcium pantothenate (0.1 M) was used as the gelation agent.

Preparing Alginate Gel Containing Metronidazole and Olive Oil, and Effect of Various Concentrations of Olive Oil on its Sustained-release Characteristics when Used The sustained-release characteristics of metronidazole in the alginate gel with oil were examined. First, a 1% sodium alginate solution was added to olive oil (0.125 g, 0.25 g, 0.5 g, 0.75 g, or 1.0 g) and metronidazole (0.25 g) (500 cps) to a total weight of 2.5 g, and the mixture was blended for 10 to 30 min. This mixture was added dropwise to 0.1 M calcium pantothenate (10 ml) and allowed to stand for 24 h to prepare hydrogel beads (oil content, 5, 10, 20, 30, and 40%). Using the gel about 24 h after the gelation, the amount of metronidazole released from the hydrogel beads was examined at various time points according to the method described in Comparative Example (FIG. 2). As a result, the sustained-release characteristics of metronidazole were found to be highest when the content of olive oil was 30% in the beads, under which condition 100% of the metronidazole was released in about 120 min.

Figure 3:
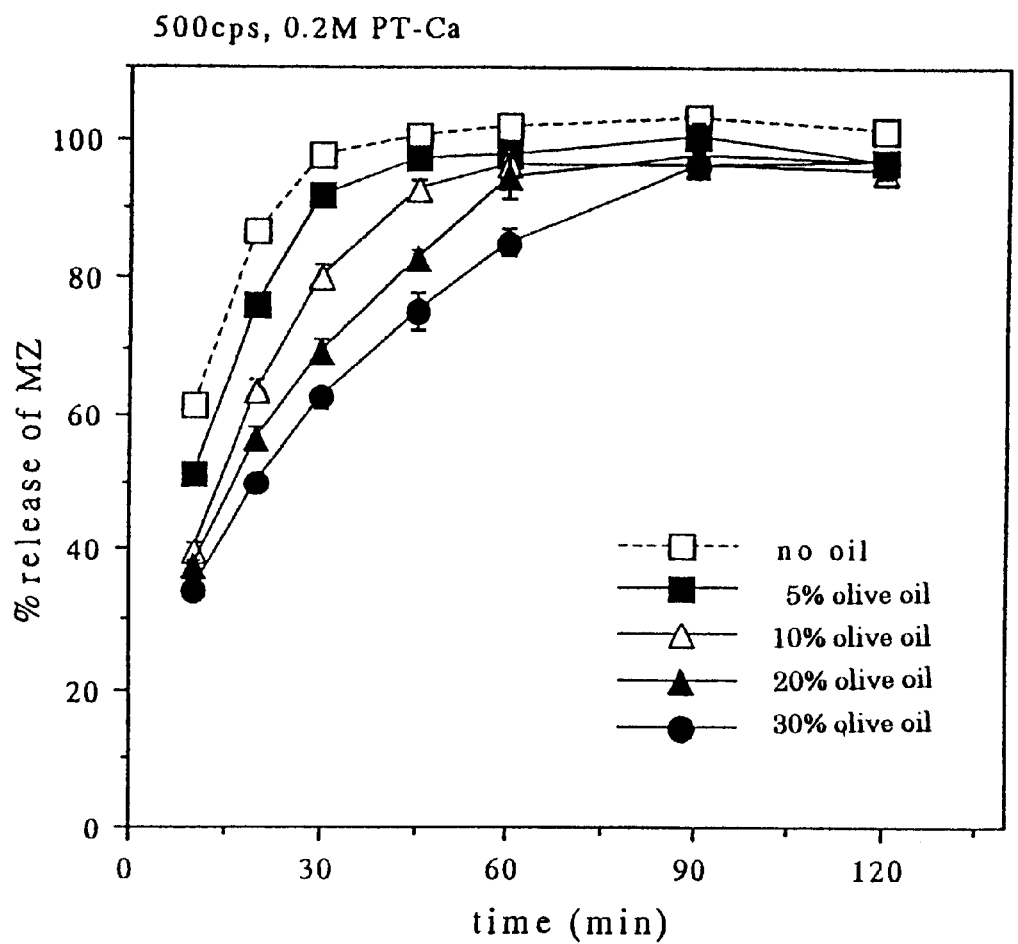
FIG. 3 is a graph showing the sustained-release characteristics of alginate gel containing metronidazole and various concentrations of olive oil. Calcium pantothenate (0.2 M) was used as the gelation agent.

Sustained-release characteristics of the drug were examined as described above except for using a 0.2 M calcium pantothenate solution as the gelation agent (FIG. 3). Almost the same results as for 0.1 M calcium pantothenate described above were obtained.

Figure 4:
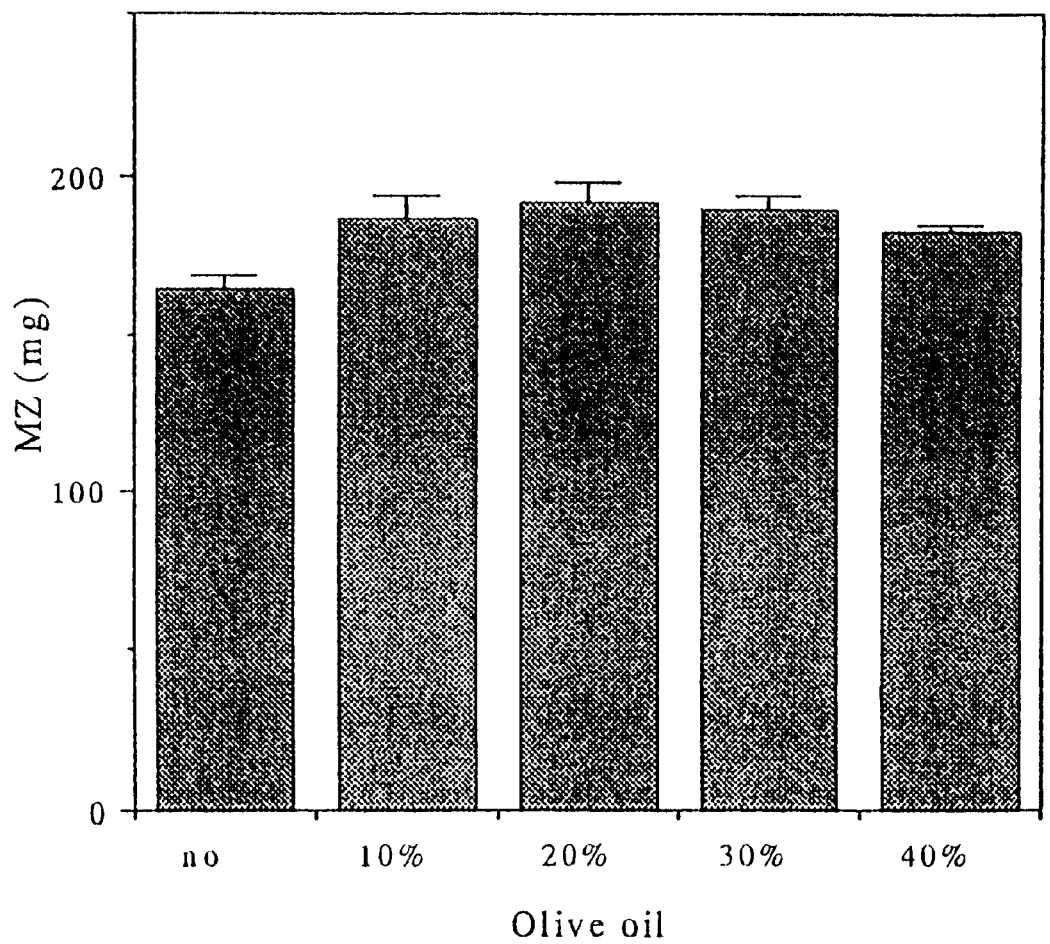
FIG. 4 is a graph showing the inclusion ratio of metronidazole into alginate gel containing various concentrations of olive oil.

Relation between oil concentrations and the ratio of metronidazole included in gels were investigated. Specifically, a 1% sodium alginate solution (500 cps) was added to olive oil (0.25 g, 0.5 g, 0.75 g, or 1.0 g) and metronidazole (0.25 g) to a total weight of 2.5 g, and the mixture was blended for 10 to 30 min. This mixture was added dropwise to a 0.1 M calcium pantothenate solution (10 ml) and allowed to stand for 24 h to prepare hydrogel beads (oil content, 10, 20, 30, and 40%). The amount of metronidazole incorporated into the gels was then determined by UV absorption spectrometry (FIG. 4). The incorporation of metronidazole into the gel was found to be significantly enhanced by adding olive oil at 10 to 30%.

EXAMPLE 2

Figure 5:
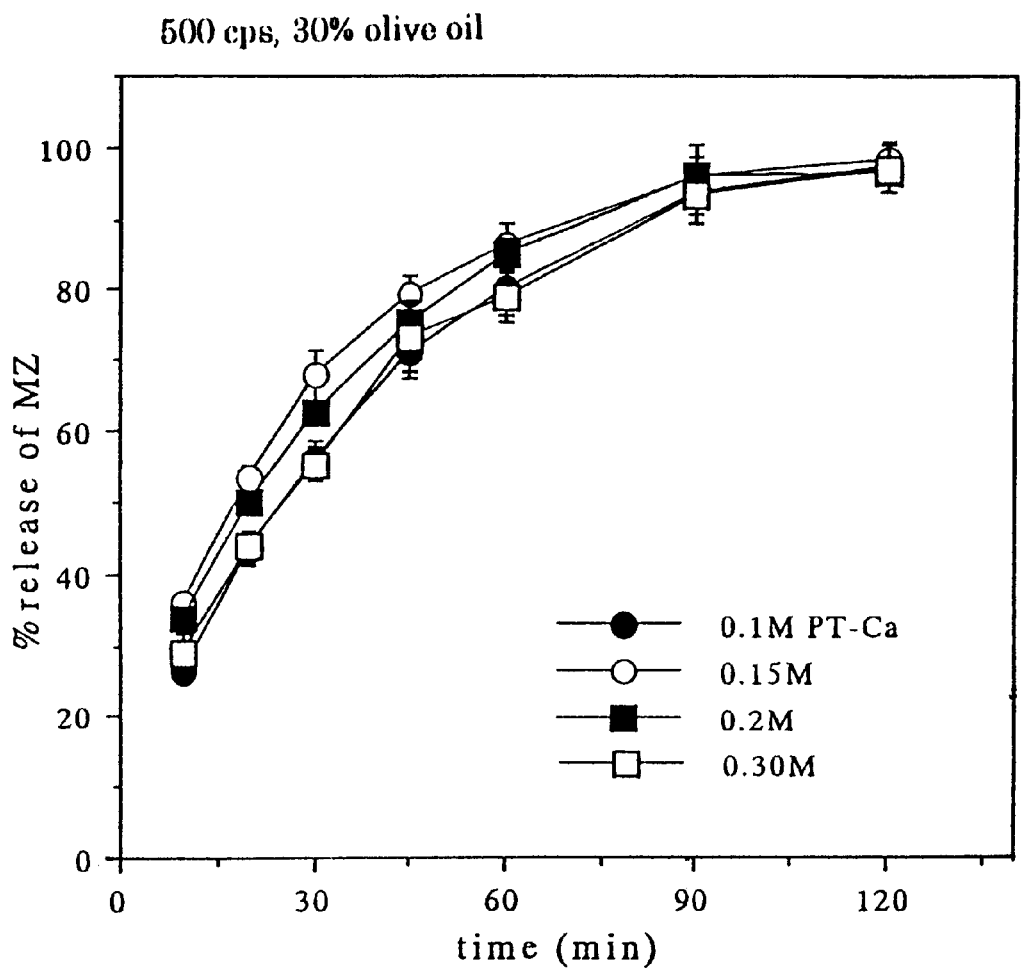
FIG. 5 is a graph showing the relation between the concentration of calcium pantothenate and the amount of metronidazole released.

Relation Between Concentrations of Calcium Pantothenate and Amount of Metronidazole Released The sustained-release characteristics were studied as in Example 1 using the gel composed of 30% olive oil and various concentrations of calcium pantothenate (0.1, 0.15, 0.2, and 0.3 M) as the gelation agent to modify the gelation status (FIG. 5). The drug sustained-release characteristics of gel were hardly affected by the difference in the calcium pantothenate concentration.

EXAMPLE 3

Figure 6:
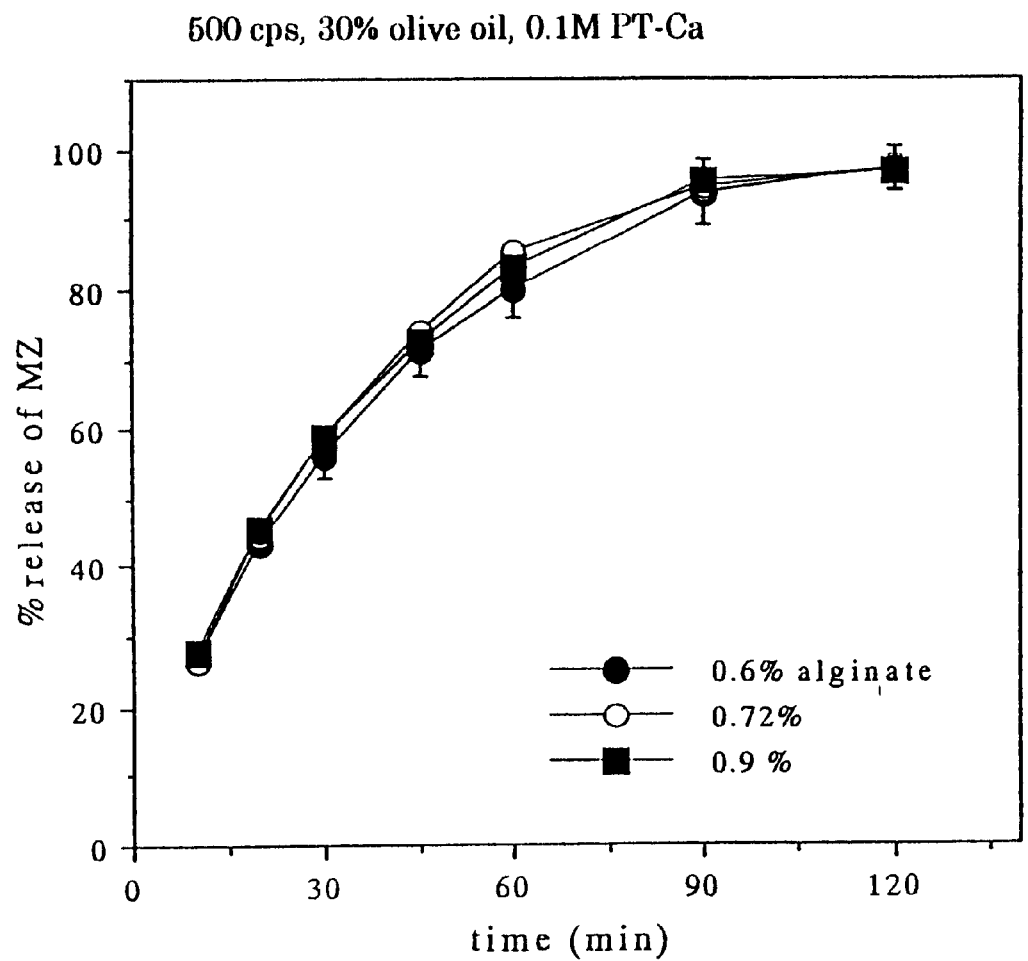
FIG. 6 is a graph showing the relation between the concentration of alginate and the amount of metronidazole released.

Relation Between Concentrations of Alginate and Amount of Metronidazole Released The sustained-release characteristics were studied as in Example 1 except for using olive oil at a concentration of 30%, 0.1 M calcium pantothenate and various concentrations of alginate (0.6, 0.72, and 0.9%) (FIG. 6). The drug sustained-release characteristics of gel were hardly affected by the differences in the alginate concentration.

EXAMPLE 4

Figure 7:
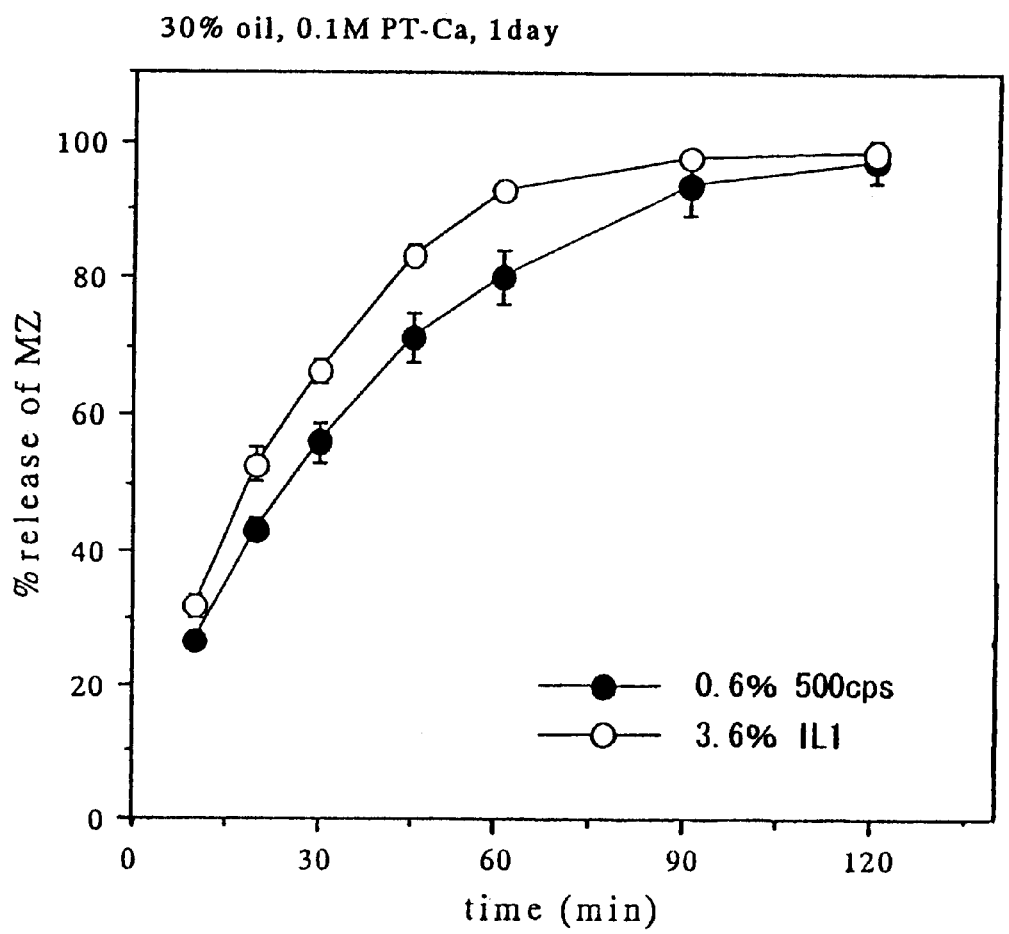
FIG. 7 is a graph showing the relation between the molecular weight of alginate and the amount of metronidazole released.

Relation Between Molecular Weight of Alginate and Amount of Metronidazole Released The sustained-release characteristics were studied as in Example 1 using a gel composed of 30% olive oil, 0.1 M calcium pantothenate, and alginates having two different molecular weights (500 cps at 0.6% and IL1 at 3.6%) (FIG. 7). As a result, it was found that the drug release could be controlled by varying the molecular weight of alginate used (the releasing rate of drug can be enhanced with a low molecular weight alginate at a high concentration). Furthermore, buoyancy of the gel was still maintained even with the alteration of molecular weight of alginate.

EXAMPLE 5

Figure 8:
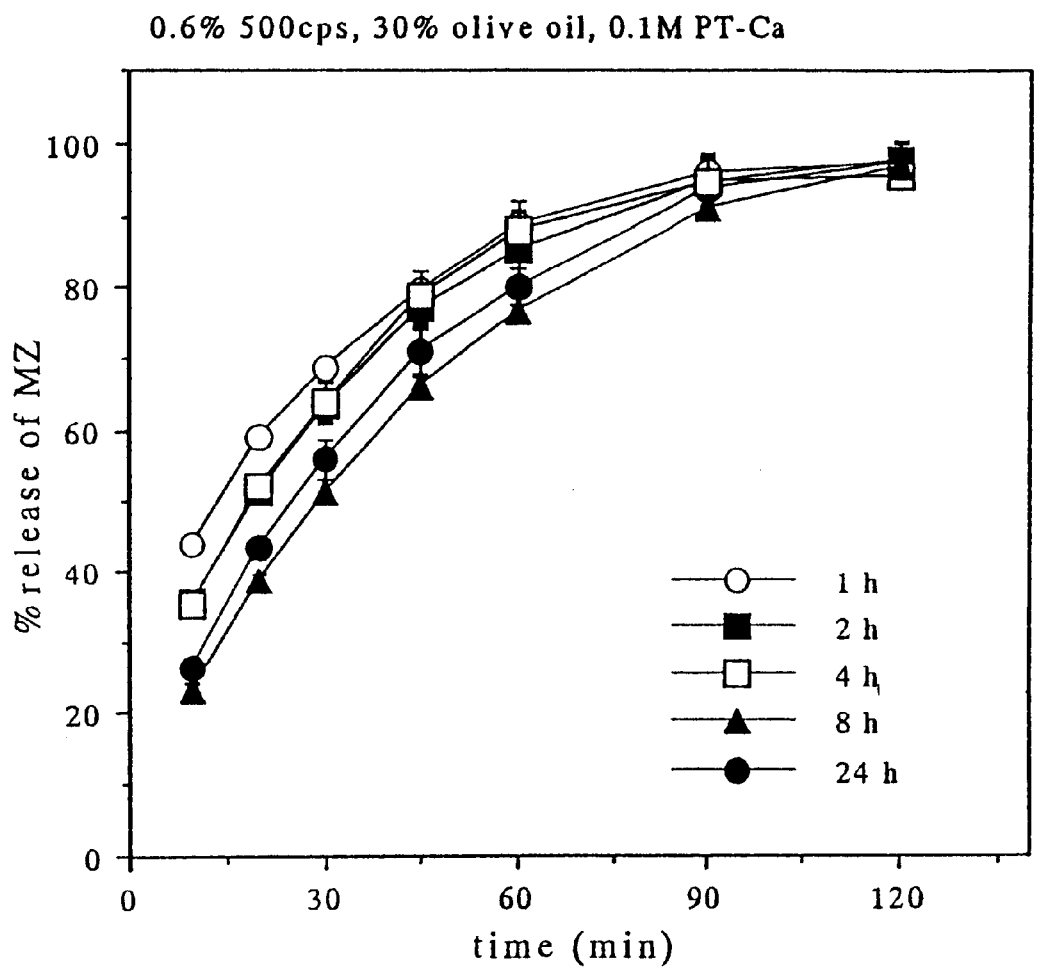
FIG. 8 is a graph showing the amount of metronidazole released from gels that differ in the time after gelation. The gels were used at 1, 2, 4, 8, and 24 h after gelation.

Study on Amount of Metronidazole Released from Gels that Differ in the Time After Gelation The sustained-release characteristics were studied as in Example 1 using a gel composed of 0.6% sodium alginate, 30% olive oil, and 0.1 M calcium pantothenate and differing gelation periods (1, 2, 4, 8, and 24 h) (FIG. 8). The initial release of the drug was found to decrease with increasing gelation time, but it reached approximately the same plateau as the gels of 8 and 24 h-gelation.

Figure 9:
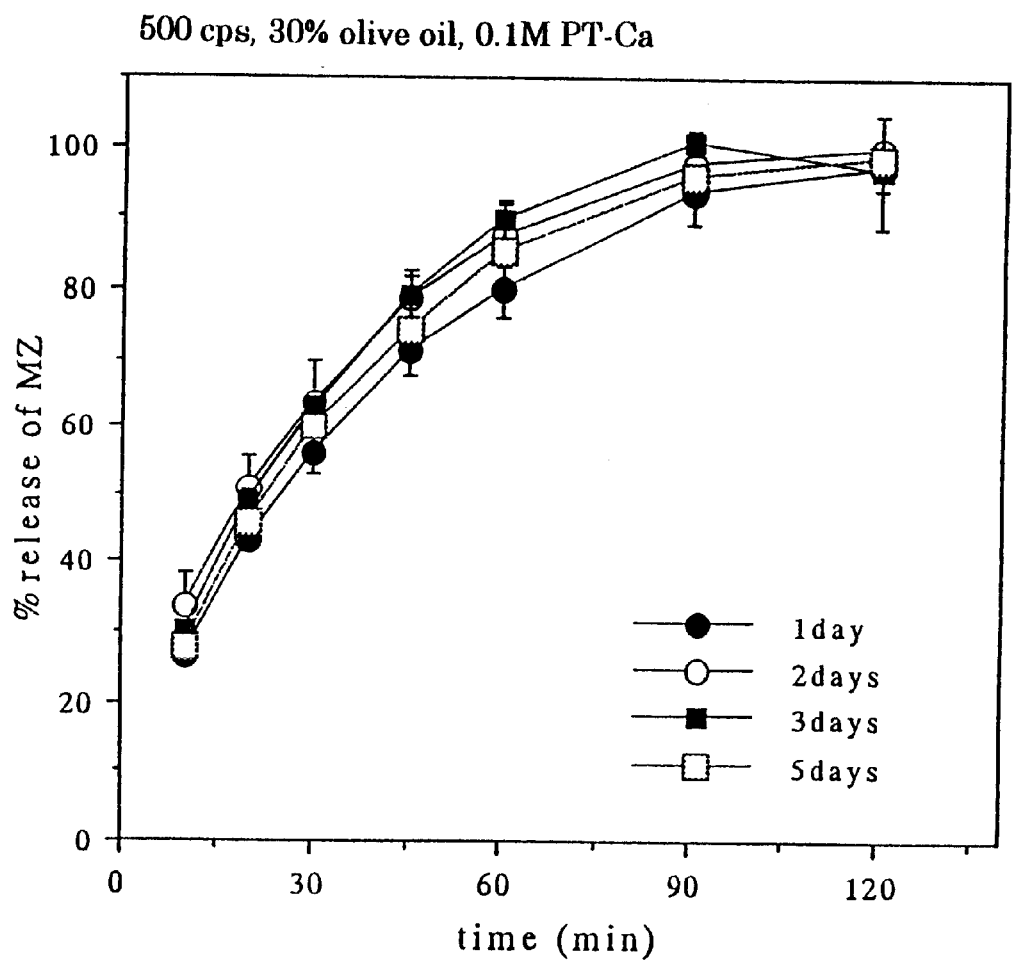
FIG. 9 is a graph showing the amount of metronidazole released from gels that differ in the time after gelation. The gels were used at 1, 2, 3, and 5 days after gelation.
Figure 10:
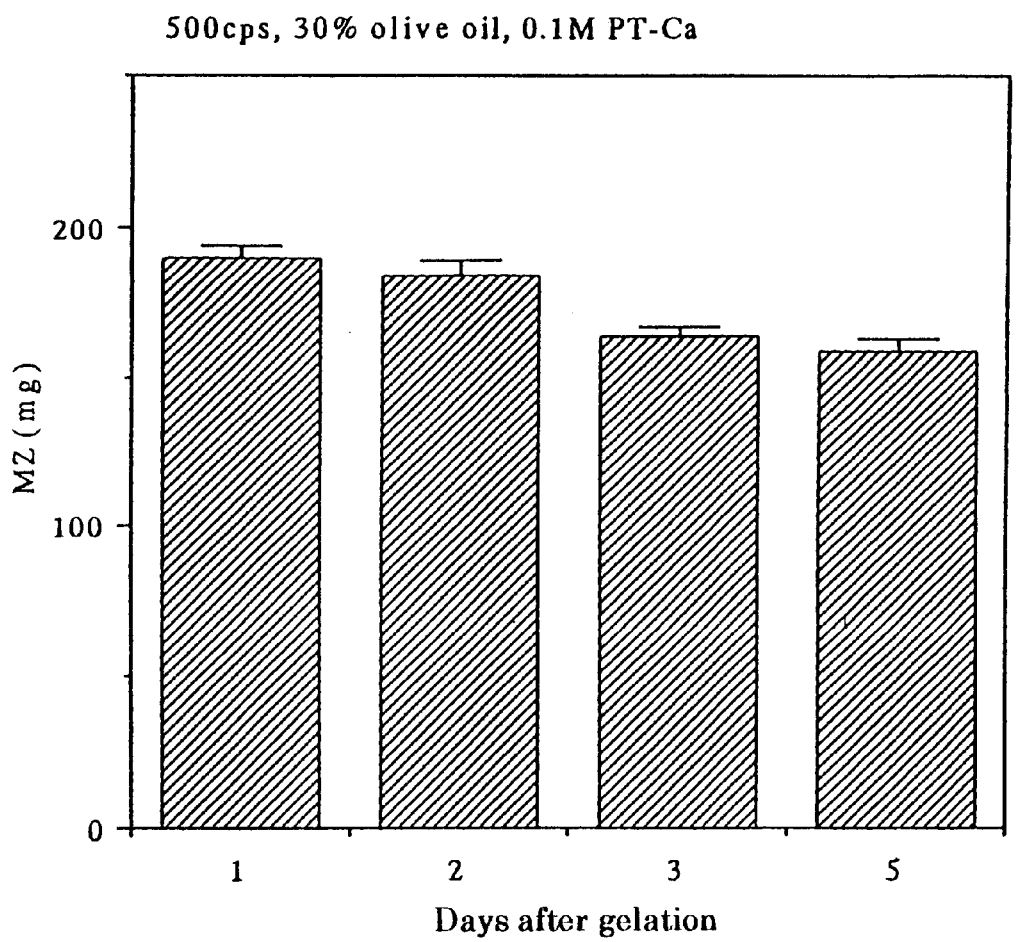
FIG. 10 is a graph showing the inclusion ratio of metronidazole into gels used at various time points after gelation. The gels were used at 1, 2, 3, and 5 days after gelation.

The sustained-release characteristics were studied as described above except for increasing the gelation period to 1, 2, 3, and 5 days (FIG. 9). As a result, similar drug-release behavior was observed with all of the gels at 1 to 5 days after the gel preparation, proving that a gelation period of 1 day (about 24 h) is sufficient for the gel preparation. In addition, the ratio of metronidazole included in the gel was examined under these conditions (FIG. 10). The inclusion ratio of metronidazole decreased especially with gels at 3 days or more after gelation. Therefore, the period of about 1 day was considered preferable as the gel preparation time.

EXAMPLE 6

Figure 11:
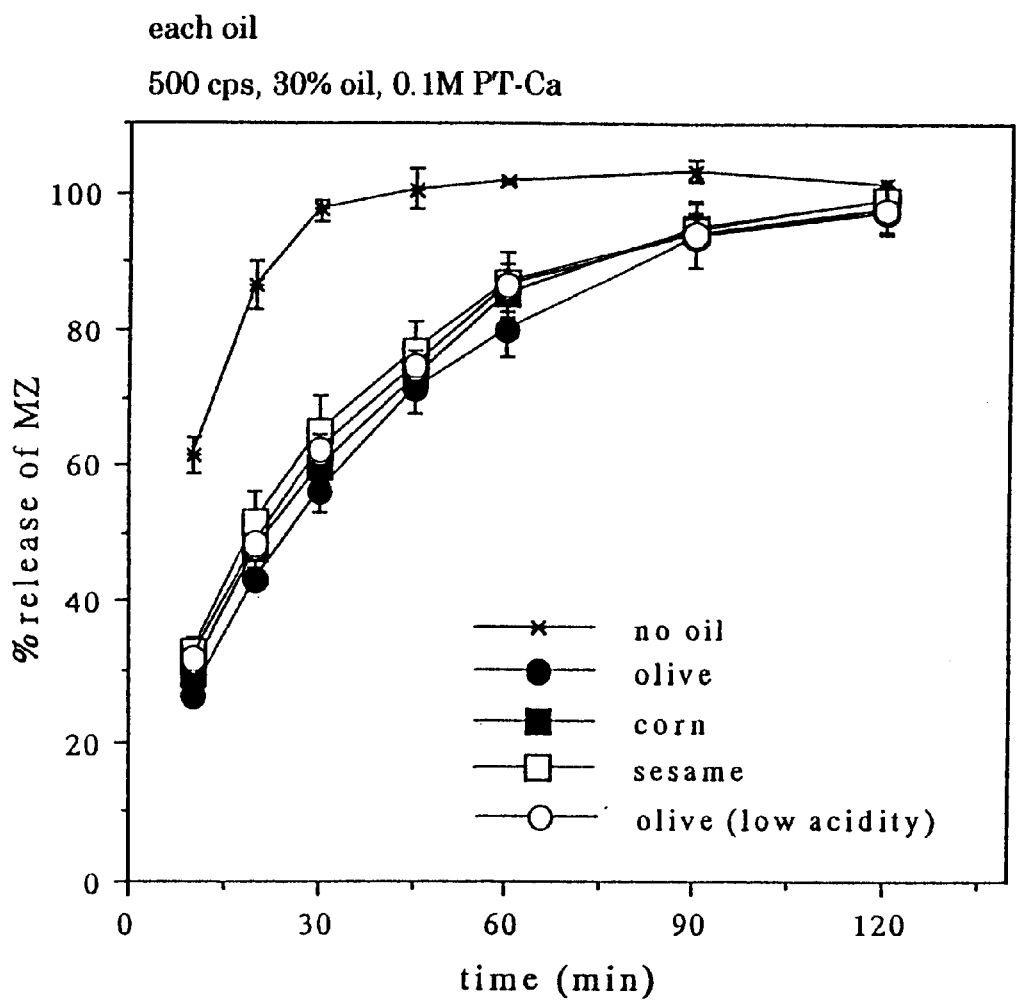
FIG. 11 is a graph showing the relation between the difference in type of oils used and the amount of metronidazole released.

Relation Between Differences in Type of Oils Used and Amount of Metronidazole Released The drug sustained-release characteristics were studied as in Example 1 using a gel composed of 0.1 M calcium pantothenate and various oils at 30% (two kinds of olive oil including oil with low acidity, corn oil, and sesame oil) (FIG. 11). Differences in the type of oils had almost no effects on the drug sustained-release characteristics of gels.

EXAMPLE 7

Buoyancy of Alginate Gel Beads

The specific gravity of test solutions (distilled water, 0.9% NaCl, and the artificial gastric juice) was determined beforehand using a standard densitometer and electronic densitometer. Gel beads containing different amounts of olive oil but no drug were prepared as in Example 1 and added to these test solutions. The number of floating beads was then counted with the naked eye (Table 1).

TABLE 1

Buoyancy of alginate gel beads containing no drug

| Olive oil (%) | Distilled water | NaCl (0.9%) Specific gravity | Artificial gastric juice |
|---|---|---|---|
| | 1.007 | 1.014 | 1.013 |
| 0 | sedimented | sedimented | sedimented |
| 5 | sedimented | sedimented | sedimented |
| 10 | floated | floated | floated |
| 20 | floated | floated | floated |
| 30 | floated | floated | floated |

Gel beads containing olive oil 10% or more were found to be buoyant. The buoyancy of beads containing 40% oil was reduced due to oil leakage, and these beads were unable to maintain a constant buoyancy. Alginate gel beads containing 30% olive oil to which metronidazole (approximately 190 mg) was incorporated as the drug were prepared as described in Example 1 and added to the above-described test solutions. The floating beads were observed with the naked eye (Table 2).

TABLE 2

Buoyancy of alginate gel beads containing drug

| Olive oil (%) | Distilled water | NaCl (0.9%) | Artificial gastric juice |
|---|---|---|---|
| 30 | sedimented → floated | floated | floated |

The gel beads containing 30% oil and the drug floated in a physiological saline (0.9% NaCl) and artificial gastric juice. These results indicate that the gel beads of the present invention can be used as a pharmaceutical preparation capable of prolonged drug release because they float in the stomach.

EXAMPLE 8

Preparing Buoyant Dried Gel Beads considering the use of the gel beads as an oral pharmaceutical preparation, buoyant dried gels were prepared as follows. A 1% sodium alginate aqueous solution containing metronidazole as a model drug and chitosan (grade F, Kimitsu Chemicals) as a natural polysaccharide was added dropwise to a 0.1 M calcium pantothenate solution at the following concentrations, and the mixture was allowed to stand for 24 h to form hydrogel beads similarly as in Example 1. These beads were fully dried at 35° C. for 6 h, and then vacuum-dried in the presence of diphosphorus pentaoxide ($P_2O_5$) to obtain dried gel beads.

The buoyancy of gel beads containing various concentrations of chitosan was examined similarly as in Example 7 (Table 3). The term "(floated)" (parenthetic "floated") in this table refers to beads which initially sedimented and then gradually became floating.

TABLE 3

| Chitosan (F) (%) | Distilled water | NaCl (0.9%) Specific gravity | Artificial gastric juice |
|---|---|---|---|
| | 1.007 | 1.014 | 1.013 |
| 0 | sedimented | sedimented | sedimented |
| 1 | sedimented | sedimented | sedimented |
| 2 | (floated) | (floated) | (floated) |
| 3 | (floated) | (floated) | (floated) |
| 5 | floated | floated | floated |

As shown in Table 3, the gel beads containing metronidazole, no natural polysaccharide, and 1% chitosan did not float at all in each solution tested. In contrast, the gel beads supplemented with 5% chitosan began floating immediately after the initiation and continued to do so until the completion of the test. However, the gels containing polysaccharides such as pullan, xylan, and agar as the natural polysaccharide did not float.

Figure 12A:
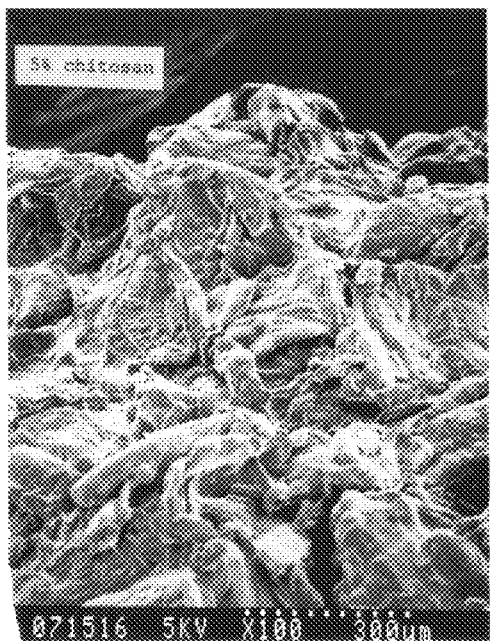
FIGS. 12A and 12B show scanning electron micrographs of the surfaces of a dried gel bead with 5% chitosan and that with 1% chitosan.
Figure 12B:
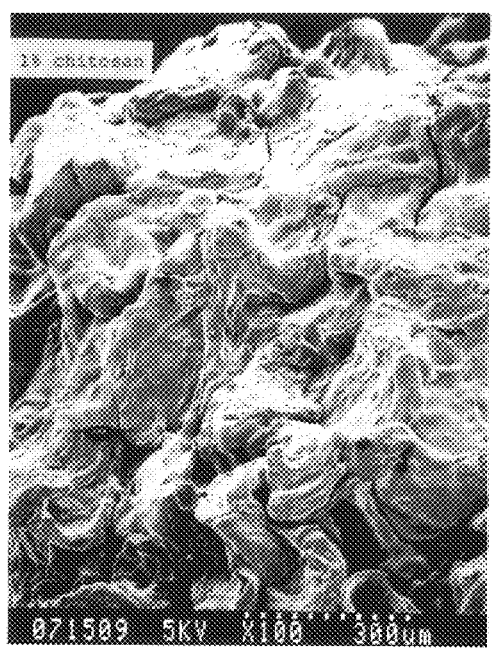

FIGS. 12A and 12B show electron micrographs of the surfaces of the buoyant dried gel beads supplemented with 5% chitosan and those supplemented with 1% chitosan with no buoyancy. Many concave and convex features are present on the surface of dried gel beads supplemented with 5% chitosan as compared with those supplemented with less chitosan (1%). These results indicate that the increased chitosan content formed many openings in the gel matrix when the gel was drying, which may have produced the buoyancy.

EXAMPLE 9

Capability of Gel Beads Containing Chitosan to Incorporate Drug

Figure 13:
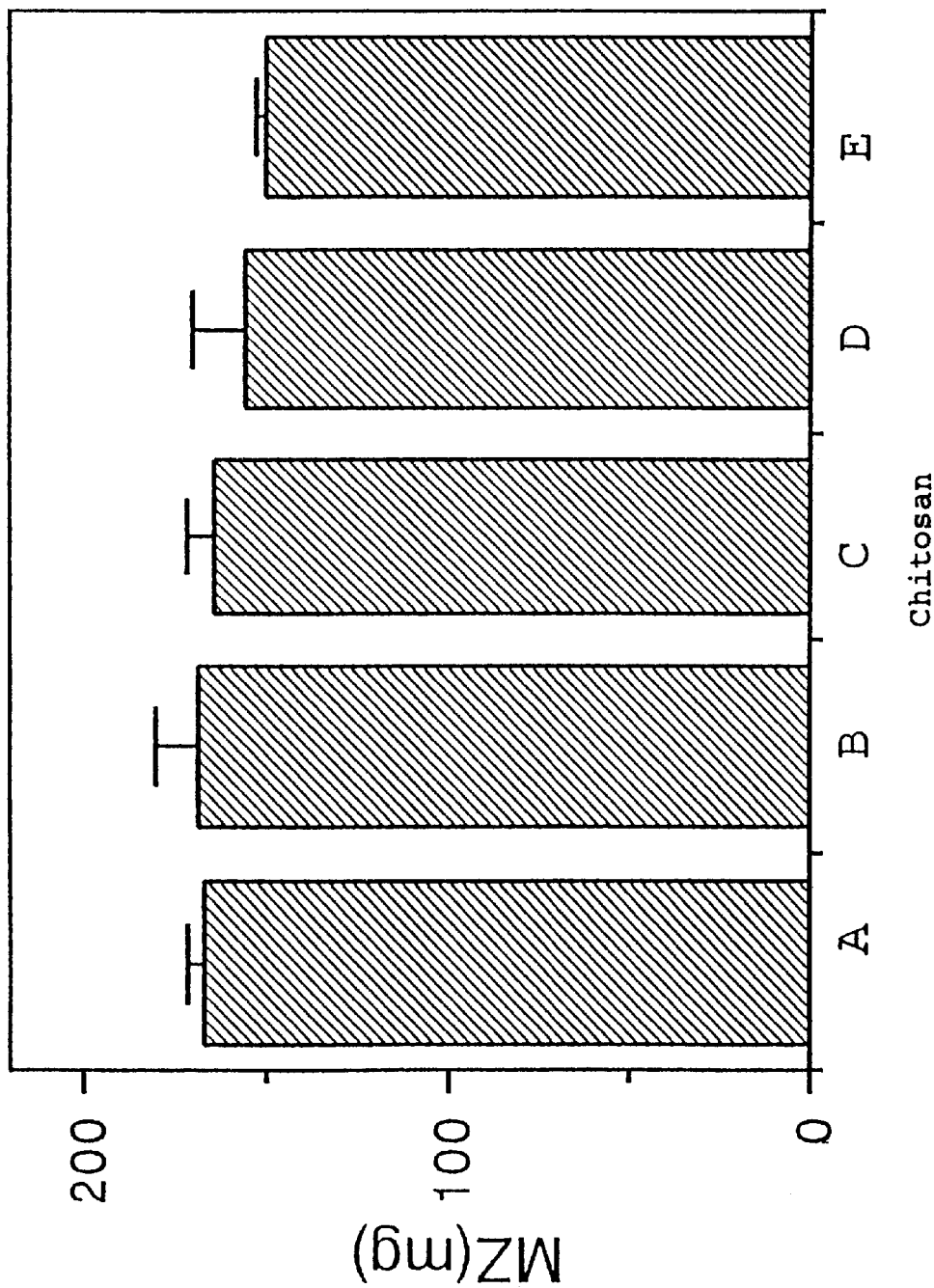
FIG. 13 is a graph showing the inclusion ratio of metronidazole in gel beads with 5% of various chitosans. Chitosans used are: A, Kimitsu (F); B, Wako (500); C, Wako (1000); D, Funakosi (10B); and E, Funakosi (7B).

Metronidazole-containing gel beads supplemented with various 5% chitosans differing in molecular weight or deacetylation extent were prepared similarly as described above, and the amount of drug incorporated into gels was measured in a similar manner as in Example 1 (FIG. 13). The molecular weight or deacetylation extent of chitosan did not significantly affect the amount of drug incorporated into gels. Similarly, the properties of various chitosans hardly affected the buoyancy of beads.

EXAMPLE 10

Release of Drug from Gel Beads Supplemented with Chitosan

Figure 14:
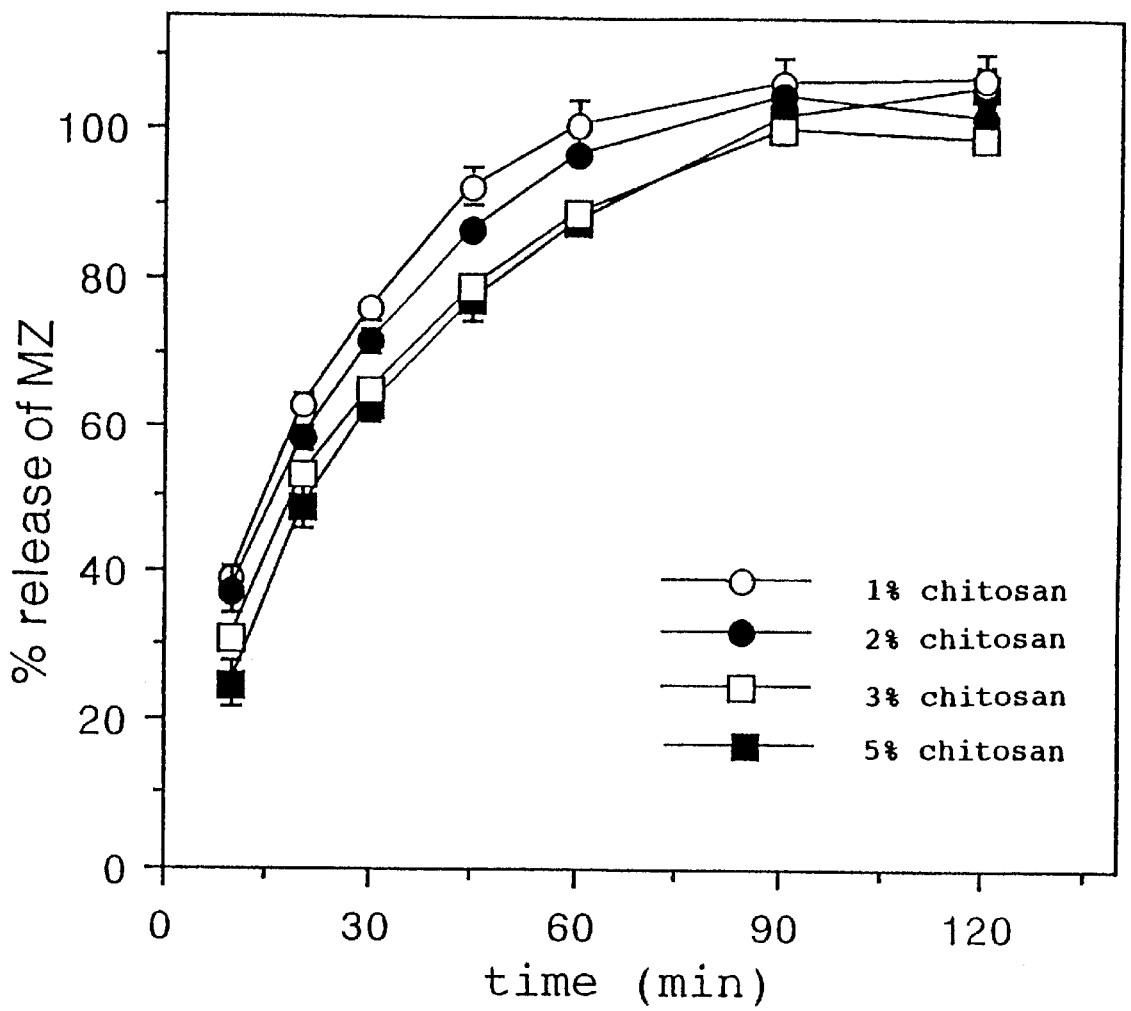
FIG. 14 is a graph showing the drug release behavior of gel beads containing metronidazole and various amounts of chitosan.

Gel beads containing metronidazole were similarly prepared as described above except for changing the amount of chitosan, and their drug dissolution release was studied in a similar manner as in Example 1 (FIG. 14). All of these beads demonstrated controlled release (sustained release) of the drug in the artificial gastric juice, and the amount of drug initially released was found to decrease as the amount of chitosan added was increased. In addition, the gel beads to which 5% chitosan was added to maintain buoyancy released 20% of the metronidazole within 10 min after the initiation of the experiment, and almost all the metronidazole in about 90 min, similarly as did the hydrogel beads containing vegetable oil.

EXAMPLE 11

Release of Drug from Gel Beads with Chitosan Added

Figure 15A:
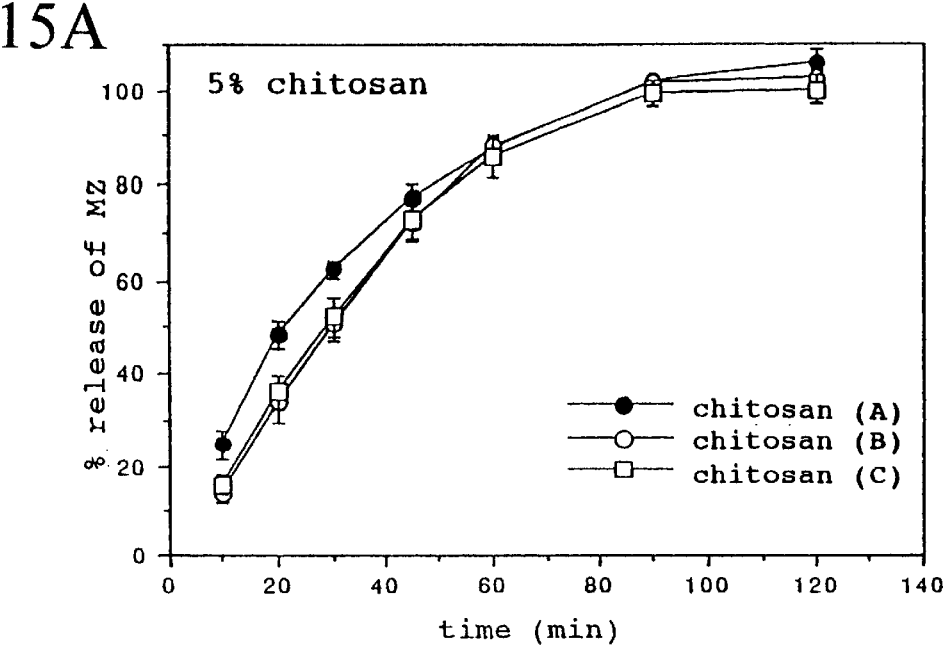
FIGS. 15A and 15B present graphs showing the drug release behavior of metronidazole-containing gel beads with 5% of the various chitosans used in FIG. 13.
Figure 15B:
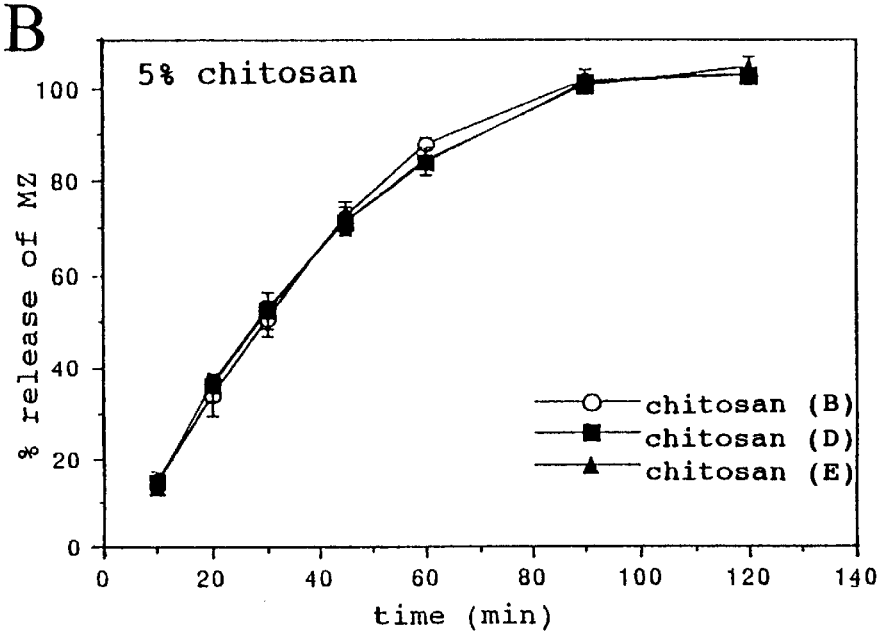

Metronidazole-containing Gel beads to which various 5% chitosans differing in molecular weight or deacetylation extent were added were similarly prepared as described above, and their drug release was studied in a similar manner as in Example 1 (FIGS. 15A and 15B). All of these beads to which different chitosens were added exhibited similar drug release properties. Furthermore, the molecular weight or deacetylation extent of chitosans had no significant effects on the amount of drug incorporated into gels. These results proved that the molecular weight or deacetylation extent of chitosan dispersed in gel matrix had almost no effects on the amount of drug released. Similar drug release behavior was also observed in chitin-containing gel beads without buoyancy.

EXAMPLE 12

Figure 16:
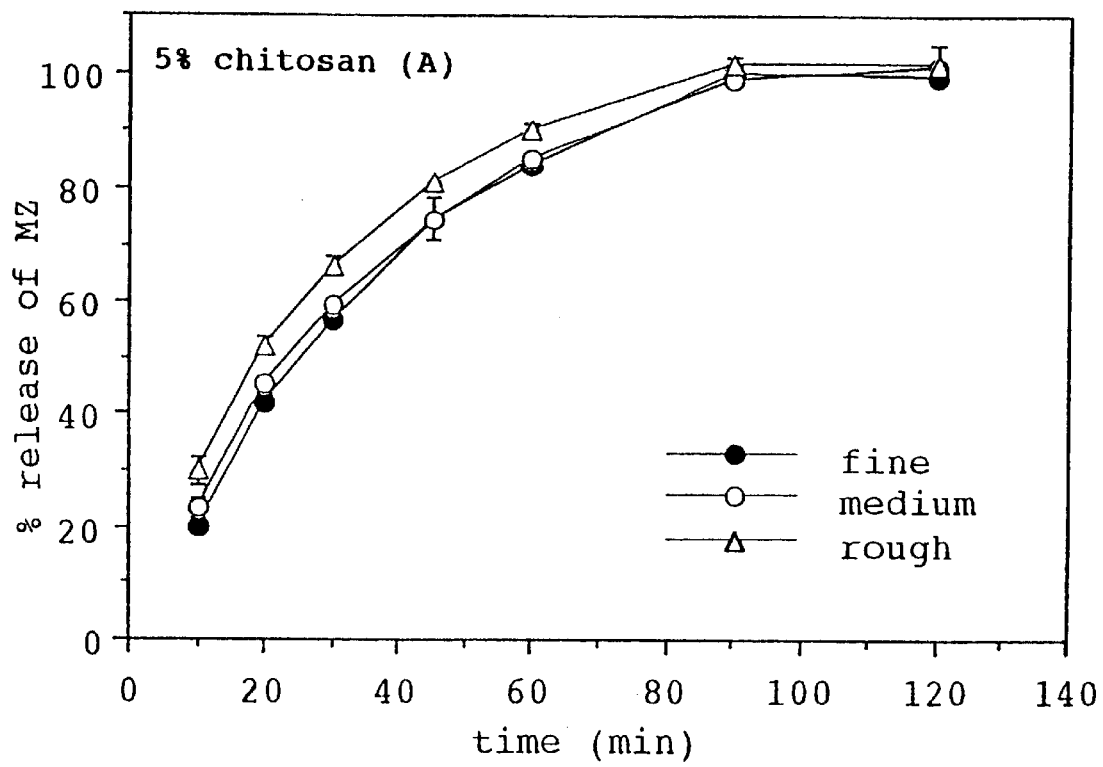
FIG. 16 is a graph showing the drug release behavior of metronidazole-containing gel beads with 5% chitosans having different particle diameters.

Effects of Chitosan Particle Diameter on Buoyancy and Drug Release Characteristic of Gel Beads with Chitosan Added Buoyancy and drug release behavior of gel beads were studied while altering the diameter of chitosan particles dispersed in the gel beads. Chitosan was first sorted using three different sized sieves (fine, medium, and coarse) to collect particles of each desired diameter. Gel beads to which 5% chitosan of different diameters was added were prepared similarly as described above. Their buoyancy (Table 4) and drug release behavior (FIG. 16) were also studied in a similar manner as described above.

TABLE 4

|  | Distilled water | NaCl (0.9%) | Artificial gastric juice |
|---|---|---|---|
|  | Specific gravity | | |
| Sample | 1.007 | 1.014 | 1.013 |
| Chitosan (fine) | floated | floated | floated |
| Chitosan (medium) | floated | floated | floated |
| Chitosan (coarse) | floated | floated | floated |
| Chitin | sedimented | sedimented | sedimented |

Stable buoyancy and approximately similar drug release behavior were observed for particles of all diameters tested.

The examples above indicate that alginate in either hydrogel or dried gel form can give particles buoyancy in the stomach, and can be applied to pharmaceutical preparations which can be suitably formulated depending on the conditions of their actual administration to human subjects. It was also indicated that hydrogel beads or dried gel beads which incorporate a drug and to which vegetable oil or chitosan is added are useful as non-degradable, long-residing pharmaceutical preparations in the stomach.

EXAMPLE 13

Measuring Drug Delivery Efficiency to the Gastric Mucosa by the Conventional Administration Method (Intraperitoneal Administration)

Conventionally, orally administered metronidazole is expected to become effective by reaching the gastric mucosa mainly via absorption by the small intestine followed by transfer into the blood stream (i.e., systemic circulation). The following experiment was performed using mice in order to measure the delivery efficiency of this drug through the blood stream to gastric mucosa by the conventional administration method.

First, an aqueous solution of metronidazole was intraperitoneally administered to 24 h-fasted ddY male mice (25 to 40 g) at a dosage of 33 mg/kg. At 0.5, 1, and 2 h after the administration, the animals underwent laparotomy under Nembutal anesthesia, and the blood was collected from posterior vena cava until death by bleeding. The blood thus collected was immediately centrifuged at 4° C. and 3600 rpm for 10 min to separate the serum, to which was added methanol to remove proteins by centrifugation. Metronidazole in the supernatant was then measured using high performance liquid chromatography (HPLC). A Cosmosil 5C18-MC column (4.6×150 mm) (NACALAI TESQUE, Inc.) in a 0.01 M phosphate buffer (pH 5.5) containing 15% methanol at a flow rate of 1 ml/min (ambient; Shimadzu LC-6A) at room temperature was used to quantify metronidazole for the HPLC measurement. Detection was performed by UV absorbency at 320 nm (detector: Shimadzu SPD-6A).

The excised stomach (about 2 $cm^2$) was washed three times with a phosphate buffer (Sorensen buffer, pH 7.4) (50 ml each) and spread on a petri dish. The gastric mucosa was then scraped off using a slide glass according to the standard method. The gastric mucosa was next suspended in said phosphate buffer (2 ml), homogenized, and centrifuged at 4° C. and 3000 rpm for 10 min. The supernatant thus obtained was then filtered through a 0.2 $\mu$m-pore membrane filter. Metronidazole contained in the filtrate thus obtained was quantitated by HPLC. Reproducibility in each procedure was confirmed by the addition and recovery test with the standard drug.

Figure 17:
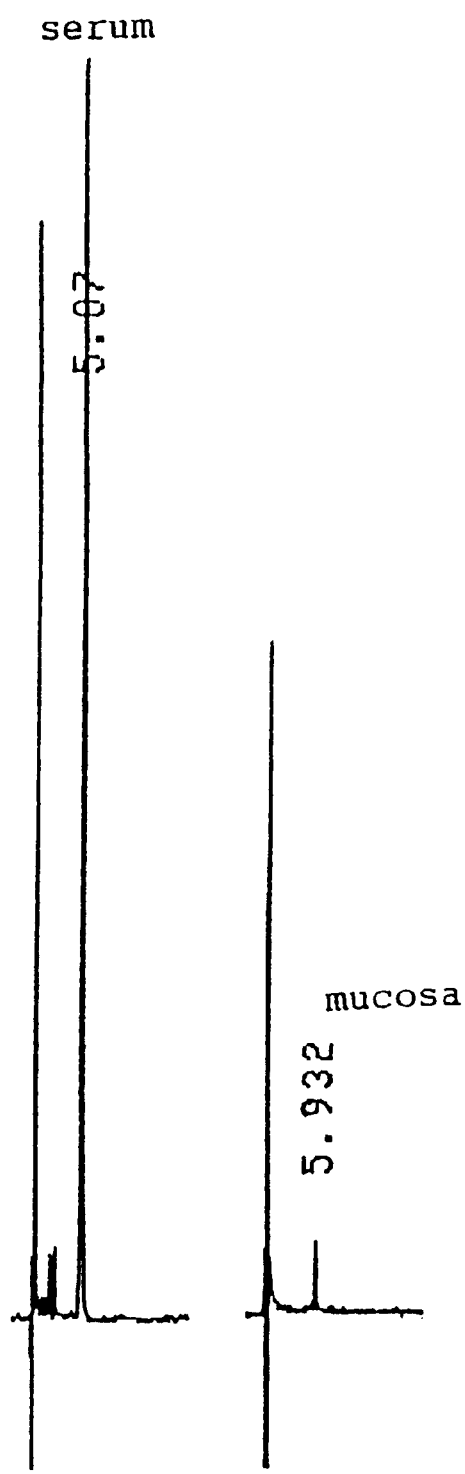
FIG. 17 shows chromatograms of metronidazole contained in serum and gastric mucosa samples collected from a mouse after the intraperitoneal administration of a metronidazole aqueous solution.
Figure 18:
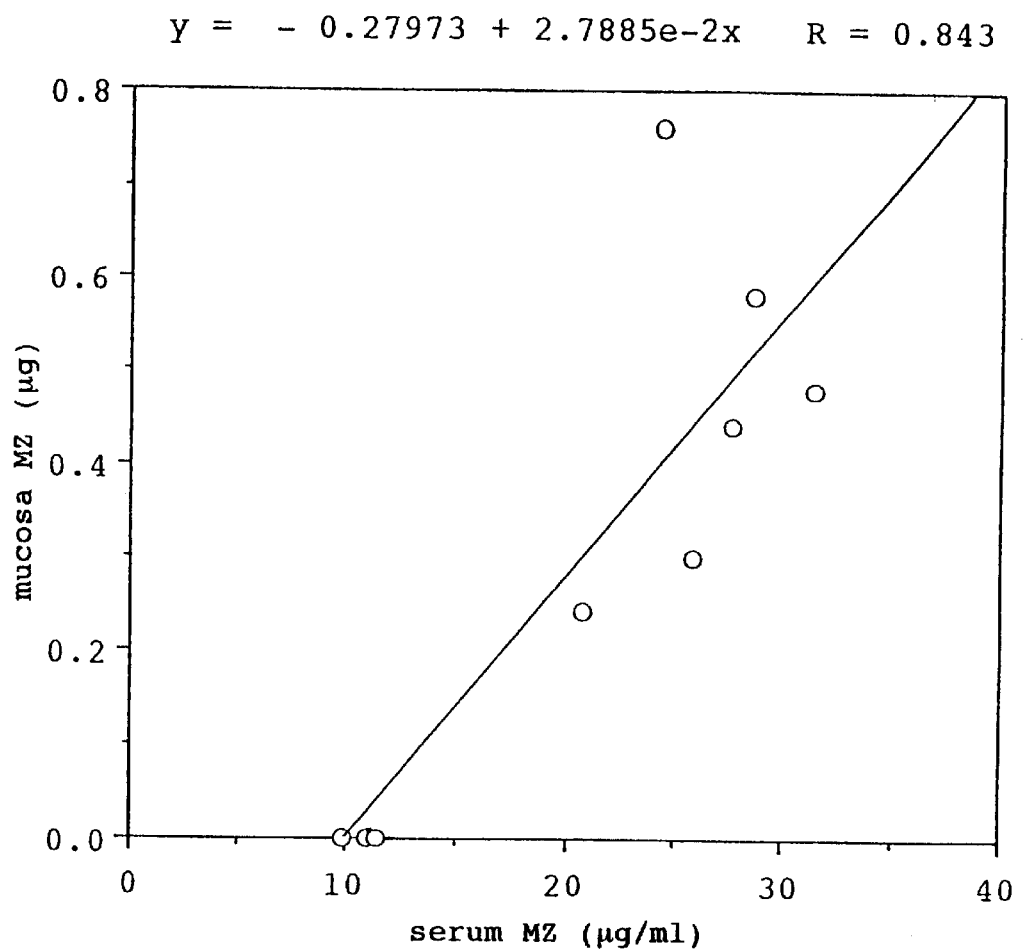
FIG. 18 is a graph showing the relation between the amounts of metronidazole contained in the serum and gastric mucosa (2 $cm^2$) samples collected from a mouse after the intraperitoneal administration of a metronidazole aqueous solution.

The results are shown in FIG. 17. Metronidazole was isolated and identified in every biological sample, and its retention time was about 6 min. The relation between the serum concentration of metronidazole and its amount in the gastric mucosa at that time in the same animal is shown in FIG. 18. As depicted in this graph, metronidazole in the gastric mucosa increased with its increase in the serum concentration, and a positive relation (r=0.843, n=9) was observed. However, it was indicated that concentrations of metronidazole higher than a certain limit are required to deliver this drug to the gastric mucosa. In addition, it was proven that, from the dosage (1 mg/30 g mouse) and the amount of metronidazole delivered into the gastric mucosa, the efficiency of drug delivery to the target tissue from the blood is extremely low when the target tissue of metronidazole is gastric mucosa. These results indicate that conventional oral pharmaceutical preparations have a low drug delivery efficiency, requiring more effective targeting techniques when the target tissue of metronidazole is gastric mucosa.

EXAMPLE 14

Measuring Efficiency of Drug Delivery to the Gastric Mucosa by Oral Administration The efficiency of drug delivery to the gastric mucosa by orally administering an aqueous solution or gel beads was studied.

Dried alginate gel beads exhibiting buoyancy and containing 5% chitosan were pulverized and sorted by particle diameter to prepare the powdered drug containing metronidazole. Twenty-four-hour-fasted mice (ddY male, 25 to 40 g) were orally administered a metronidazole solution (1 mg/30 g body weight) or a suspension of the above-described dried and pulverized alginate gel beads containing chitosan 5% (including 1 mg/30 g body weight metronidazole) using a probe. At 0.5, 1, 2, 3, and 4 h after the administration, the animals underwent laparotomy under Nembutal anesthesia, and the blood was collected from the posterior vena cava until death by bleeding. The blood thus obtained was centrifuged (4° C., 3600 rpm, 10 min) to separate serum, to which was added methanol to remove proteins by centrifugation. Metronidazole in the supernatant was then measured using high-performance liquid chromatography (HPLC). The HPLC measurement was performed under similar conditions to those in Example 13. The excised stomach (about 2 cm$^2$) was washed three times with a phosphate buffer (Sorensen buffer, pH 7.4) (50 ml each) and spread on a petri dish. The gastric mucosa was then scraped off using a slide glass. The gastric mucosa was homogenized in said phosphate buffer (2 ml) and centrifuged (4° C., 3600 rpm, 10 min). The supernatant thus obtained was filtered through a membrane filter, and then metronidazole in the filtrate was measured by HPLC. Reproducibility in each procedure was confirmed by the addition and recovery test with the standard drug.

Figure 19A:
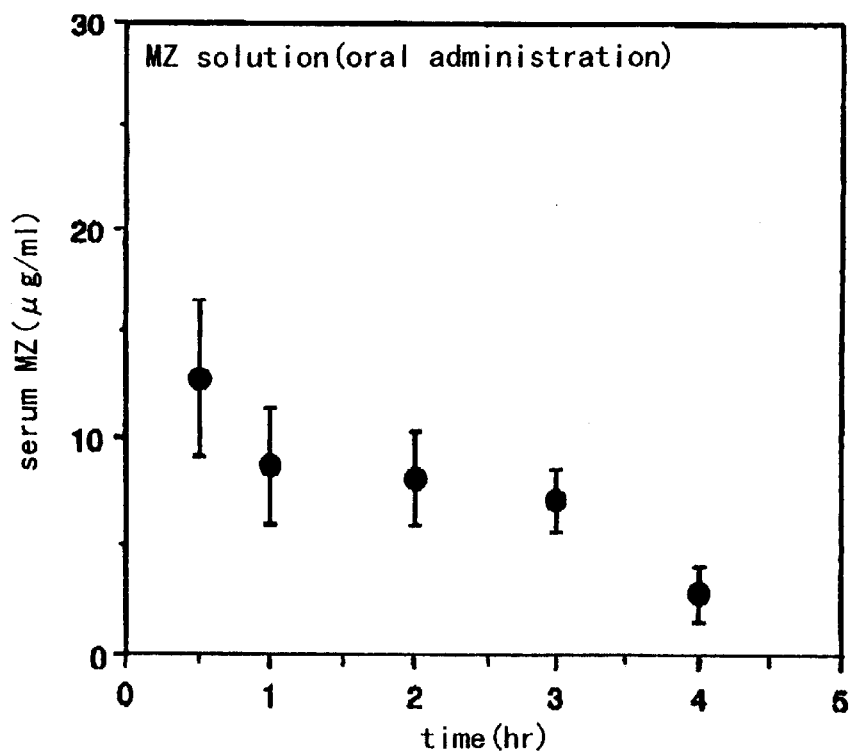
FIGS. 19A and 19B presents graphs showing the time course of changes in the amount of metronidazole contained in the serum and gastric mucosa samples collected from a mouse after the oral administration of a metronidazole aqueous solution.
Figure 19B:
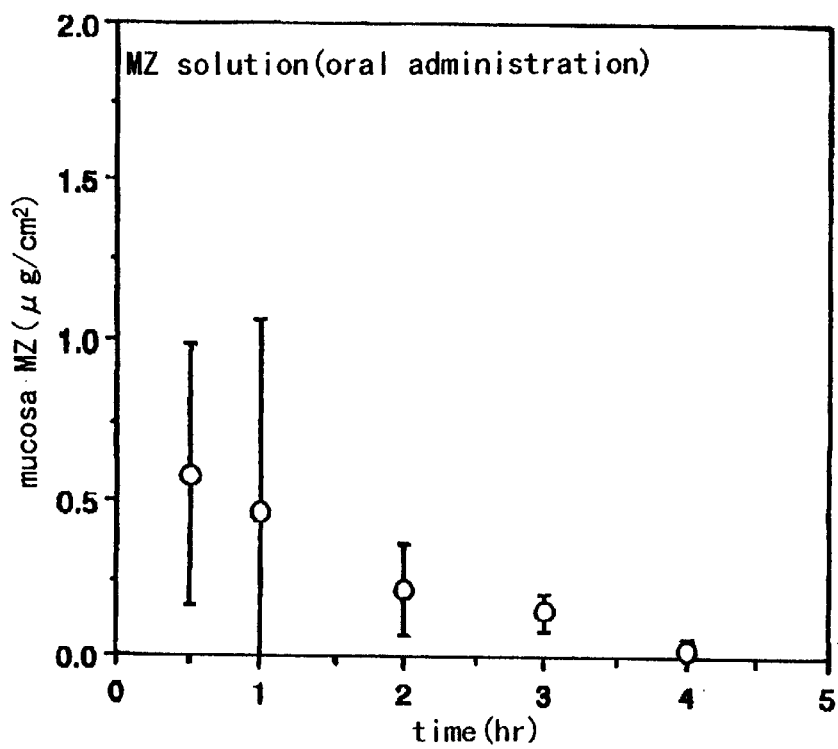

Results of measuring the drug delivery efficiency of an aqueous solution of metronidazole administered orally are shown in FIGS. 19A and 19B. It was proved that metronidazole was quickly absorbed when its aqueous solution was orally administered. All data obtained for oral administration were compared with the data obtained for intraperitoneal administration at the same dose, and the amount of drug delivered to the gastric mucosa was predicted from its concentration in the blood. The oral administration method delivered significantly more drug. Furthermore, metronidazole became undetectable in the gastric mucosa 2 h after intraperitoneal administration as determined by its disappearance in the blood. In contrast, the drug was present in the mucosa up to 4 h after its oral administration.

These results might have been caused not only by drug delivery from the blood to the gastric mucosa but also by direct delivery of the drug to the gastric mucosa from the stomach cavity during its endogastric passage.

Figure 20A:
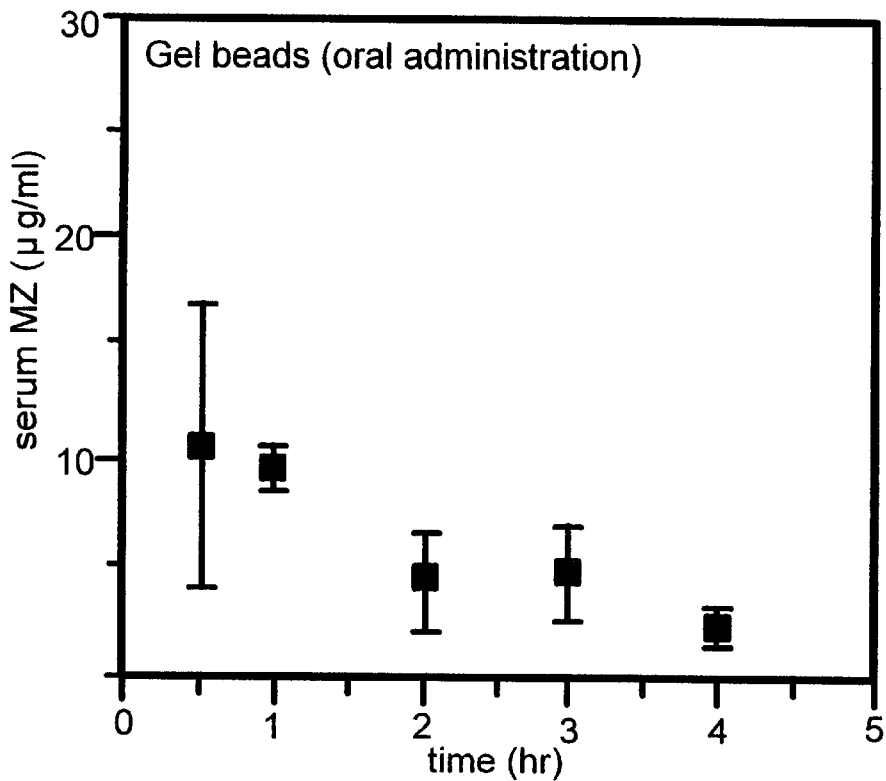
FIGS. 20A and 20B show graphs describing the time course of changes in the amount of metronidazole contained in the serum and gastric mucosa samples collected from a mouse after the oral administration of metronidazole incorporated in chitosan-containing dried gel beads.
Figure 20B:
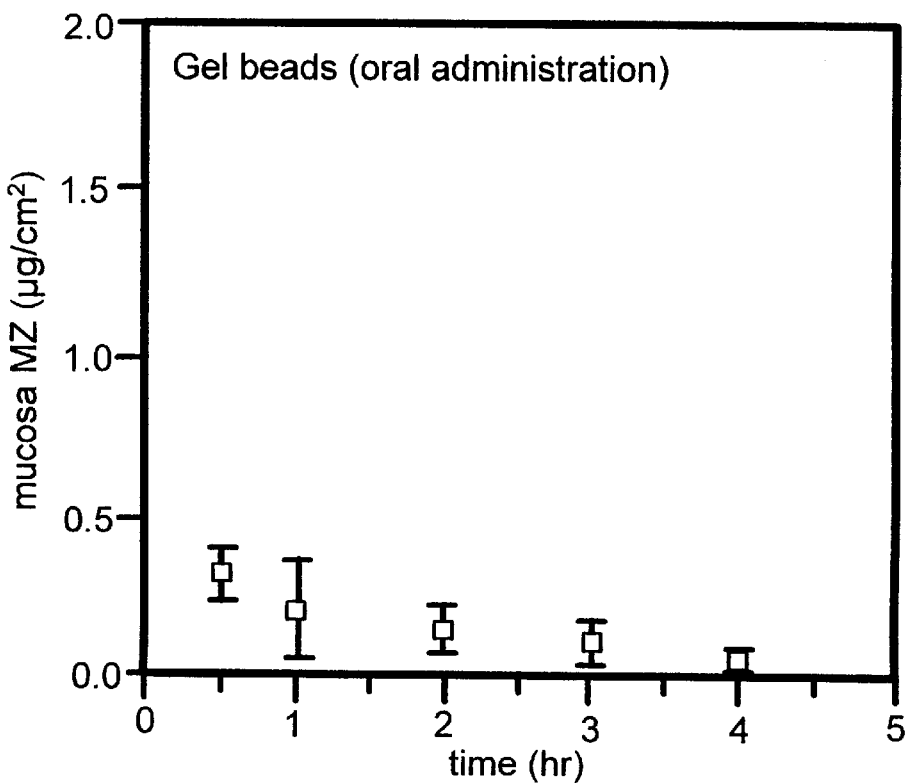

The results of orally administering dried gel beads containing chitosan are shown in FIGS. 20A and 20B. Profiles of metronidazole concentration in blood due to bead administration showed a similar tendency to those by the administration of the aqueous solution, confirming the accurate release of the model drug even from a pharmaceutical preparation composed of gel matrix. Furthermore, significantly more drug was delivered to the gastric mucosa by oral administration than by intraperitoneal administration. However, no significant difference in the amount of orally administered metronidazole delivered to the gastric mucosa was observed as compared with that by administration of its aqueous solution.

EXAMPLE 15

Measuring Efficiency of Drug Delivery to Gastric Mucosa in Guinea Pigs by Oral Administration Forty-eight-hour-fasted guinea pigs (Hartley male, 500 to 950 g) were administered an aqueous solution of metronidazole (15 mg/kg body weight) or four dried alginate beads with 5% chitosan (containing 15 mg/kg metronidazole) into the stomach using a probe. At predetermined times after the administration, laparotomy was performed under Nembutal R anesthesia, and the blood was collected from the abdominal aorta until death by bleeding. The blood thus obtained was centrifuged to separate the serum, proteins were removed with methanol, and metronidazole contained in the supernatant was measured using HPLC. The HPLC measurement was carried out under similar conditions to those used in the mouse experiments. The excised stomach was washed four times with a phosphate buffer (Sorensen buffer, pH 7.4) (50 ml each) and spread on a petri dish. After the spread area was measured, the gastric mucosa was scraped off using a slide glass, homogenized in said phosphate buffer (3 ml), and centrifuged. The supernatant thus obtained was centrifuged after a further addition of methanol, and the resulting supernatant was assayed for the amount of metronidazole by HPLC. In this case of oral administration of gel beads, the buoyancy and number of beads remaining in the stomach were observed.

Autopsy results confirmed that half or more of the beads administered were retained floating in the stomach 3 hours after the administration of gel beads. In addition, this pharmaceutical preparation did not adhere to the internal surface of the stomach at all. At 3 hours, the concentration of metronidazole in the blood was 4.0±2.0 µg/ml, and the amount delivered to the gastric mucosa was 22.8±10.3 µg/stomach.

Three hours after the oral administration of the aqueous solution containing the same amount of metronidazole, its concentration in the blood was 4.8±3.5 µg/ml, and its amount delivered to the gastric mucosa was 4.6±5.5 µg/stomach, proving that the efficiency of drug delivery to the gastric mucosa was low in spite of the presence of about the same amount of drug in the blood as compared with the administration of floating gel beads. These results coincide with those obtained in the mouse experiments.

The above results indicate that alginate gel supplemented with chitosan, which has a longer residence time than the aqueous solution and continuously releases drug in the stomach, more efficiently delivers metronidazole used as the model drug to the gastric mucosa, directing it to the target tissue.

What is claimed is:

1. A gel composition comprising a compound to be sustainedly released, an alginate gel, and a polysaccharide, wherein said polysaccharide is chitosan and wherein said gel and said polysaccharide are present in an amount effective to confer buoyancy in gastric juice on said gel composition.

2. The gel composition according to claim 1, wherein said compound to be sustainedly released is a drug.

3. The gel composition according to claim 2, wherein said drug is for treating diseases of digestive organs.

4. The gel composition according to claim 1, wherein the amount of chitosan is about 5%.

5. The gel composition according to claim 1, wherein the amount of said alginate gel is from about 0.5% to about 20%.

* * * * *

UNITED STATES PATENT AND TRADEMARK OFFICE
CERTIFICATE OF CORRECTION

PATENT NO. : 6,284,745 B1
DATED : September 4, 2001
INVENTOR(S) : Susumu Kawashima and Yoshifumi Murata It is certified that error appears in the above-identified patent and that said Letters Patent is hereby corrected as shown below:

Column 9,
Line 4, "chitosens" should read -- chitosans --.

Signed and Sealed this

Seventh Day of May, 2002

Attest:

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.    : 6,284,745 B1
DATED         : September 4, 2001
INVENTOR(S)   : Susumu Kawashima, Yoshifumi Murata It is certified that error appears in the above-identified patent and that said Letters Patent is hereby corrected as shown below:

<u>Title page,</u>
Item [73], Assignee: "Meiji Milk Products Co., Ltd. (JP)" should read -- Meiji Milk Products Co., Ltd. (JP); Susumu Kawashima (JP) --.

Signed and Sealed this

Eleventh Day of June, 2002

*Attest:*

JAMES E. ROGAN
*Attesting Officer*    *Director of the United States Patent and Trademark Office*